United States Patent
Tsubouchi

(10) Patent No.: US 7,115,388 B2
(45) Date of Patent: Oct. 3, 2006

(54) PRODUCTION OF FUNCTIONAL POLYPEPTIDES ORIGINATING FROM SILK PROTEIN AND USE THEREOF

(75) Inventor: Kozo Tsubouchi, Ibaraki (JP)

(73) Assignee: National Institute of Agrobiological Sciences, Tsukuba (JP)

( * ) Notice: Subject to any disclaimer, the term of this patent is extended or adjusted under 35 U.S.C. 154(b) by 188 days.

(21) Appl. No.: 10/798,158

(22) Filed: Mar. 11, 2004

(65) Prior Publication Data

US 2004/0219630 A1    Nov. 4, 2004

(30) Foreign Application Priority Data

Mar. 14, 2003    (JP)    ............................. 2003-071035

(51) Int. Cl.
*C12P 21/06*    (2006.01)

(52) U.S. Cl. ................... 435/68.1; 514/12; 530/350

(58) Field of Classification Search ............... 435/68.1; 514/12; 530/350, 69.1

See application file for complete search history.

*Primary Examiner*—Robert A. Wax
*Assistant Examiner*—Robert B. Mondesi
(74) *Attorney, Agent, or Firm*—Flynn, Thiel, Boutell & Tanis, P.C.

(57) ABSTRACT

It is an object to provide polypeptide compositions originating from silk protein which have not only excellent cell growth-promoting activity associated with undegraded silk fibroin and sericin, the fibroin H-chain and L-chain, or the a component of sericin, but also excellent touch, extensibility, and the like inherent in fibroin and sericin having a molecular weight not higher than 200,000. A method for producing functional polypeptide compositions originating from silk protein having an average molecular weight not lower than 10,000 and not higher than 200,000 and being excellent for cell growth-promoting activity, extensibility and the like, comprising; solubilizing a raw silk protein material from the domesticated silkworm or *Antheraea yamamai* in an aqueous solution of neutral salt, the raw silk protein material having an average molecular weight larger than 200,000 and at least a part or the whole of the H-chain and L-chain of silk fibroin and sericin a left undegraded in the case of the raw silk protein material from the domesticated silkworm; treating subsequently the solution with a peptide bond-cleaving agent; and cleaving peptide bonds between specific amino acid residues of silk protein.

8 Claims, 2 Drawing Sheets

Electrophoretogram
M: Marker
H: Fibroin H-chain
L: Fibroin L-chain

Electrophoretogram
M: Marker (for low molecular weight)
a, d, b, c: Each component of sericin

PRODUCTION OF FUNCTIONAL POLYPEPTIDES ORIGINATING FROM SILK PROTEIN AND USE THEREOF

BACKGROUND OF THE INVENTION

1. Field of the Invention

The present invention relates to functional polypeptide compositions originating from silk protein excellent for promoting cell growth, extensibility and the like, a production method thereof and use thereof in the fields of medicament, quasi drug, cosmetics as a material for skin care, food and the like.

2. Description of the related Art

Since silk threads have been used as a surgical suture from the old days, silk protein is regarded as a biocompatible material, and developments have recently become active for new uses of silk threads in various fields other than that of clothing.

For example, as available fields, silk threads are solubilized to form an aqueous silk protein solution, followed by conversion to powder by coagulation, drying, grinding, etc., for additives of cosmetics; the aqueous silk protein solution is made into a film-like material by casting on a plate and the like for cell culture bed, wound-covering and coating material; and the aqueous silk protein solution is made into a gel-like material for use in food and cosmetics. The developments of these uses are pursued (see Patent literatures 1 to 11).

As described above, silk materials are processed and used in the forms of powder, film, gel and the like after silk threads are solubilized to form an aqueous silk protein solution.

In the processes of these silk materials, neutral salt is mainly used for solubilizing silk threads. However, there is no description that the aqueous solution of neutral salt of silk protein has a property of human cell growth promotion.

Further, during the development of new silk materials, it has come to be said that silk protein has a variety of functions such as cell growth, antioxidation, germicidal action, alcohol digestion and anticoagulation of blood.

The present inventors paid attention to the cell growth function associated with silk protein and have pursued the development and study of understanding of its function with the aim of utilizing cocoon filaments or silk threads as a skin care material for wound-covering materials and cosmetics after these are solubilized and then converted into powder, film, gel and the like (see Patent literatures 12 to 14).

Furthermore, the present inventors had separated, purified and recovered the components constituting silk protein and evaluated their functions, studying which site or structure in silk protein was responsible for the cell growth function. As the result, it was found that the fibroin H-chain (see Patent literature 15) and L-chain (see Patent literature 16) and the a component of sericin (see Patent literature 17), both constituting silk protein, have a growth-promoting action on fibroblasts originating from normal human skin.

They are particularly excellent for cell adhesion in the cell growth process.

Fibroin in which the H- and L-chains are held together via SS bonds having a molecular weight of 370,000 daltons and the sericin a having a molecular weight of 400,000 daltons are called undegraded silk protein.

On the other hand, silk threads are used for fiber, besides the field of clothing, in the fields of medical care (surgical suture for surgery), cosmetics (puff) and the like.

It has recently been recognized that the molecular weight of silk protein decreases during these processes of cocoon and raw silk.

Moreover, in the processes of converting cocoon filaments or silk threads into powder, film, gel and the like (particularly, the solubilizing process of cocoon filaments or silk threads), the molecular weight of silk proteins was found to decrease (see Patent literatures 18 and 19).

An electrophoretogram of silk protein with molecular weight decreased by conventional processes of silk shows only a broad band with a smear in a molecular weight range between 10,000 and 200,000 daltons.

Degraded products of silk protein having lower than ca. 5,000 daltons are eliminated during the processes of dialysis and the like. Therefore, it is considered that the molecular weight of silk protein has been decreased up to amino acid and peptide levels during the processes. Here, polypeptide means having amino acid residues not less than 30 and peptide means having amino acid residues less than 30.

In addition, it has been found that silk proteins with reduced molecular weights in such ways are reduced in growth-promoting activity for human cells (see Patent literature 14). As to the cell growth rates of silk fibroin and sericin, they show highest values in their undegraded states. When an average molecular weight is decreased to about 200,000 daltons, the cell growth rate becomes about half of that at the time when they are in undegraded states, and when the molecular weight is decreased to 20,000 to 40,000 daltons, the cell growth-promoting activity is hardly present.

This reason may be that substances inhibiting cell growth are generated as their molecular weights are reduced.

As to the reasons for the inhibition of cell growth by silk protein, it is considered that peptide bonds of protein are generally cleaved in a complex fashion and heterogeneously by acid, alkali, light (ultraviolet light, radiation and the like), heat or the like, thereby reducing its molecular weight, or that modification of the side chains of amino acid residues (oxidization, halogenation, deamidation or the like) takes place, or the like.

In other words, treatment with acid, alkali, light, heat or the like during the steps of silk processing causes reduction in the molecular weights due to cleavage of nonspecific peptide bonds as well as increased inhibition of cell growth in spite of excellence for cell growth promotion of undegraded fibroin and sericin.

Accordingly, in order to use the function of cell growth promotion of silk protein, it is preferred to use undegraded silk fibroin, sericin, the H-chain (about 350,000 daltons) and L-chain of fibroin, sericin a (about 400,000 daltons), or the like.

However, when the physical properties of silk protein are taken into consideration, fibroin and sericin in solution have properties that the higher the molecular weights of fibroin and sericin are, the more easily they become fibers (crystallization) by shear at the time of vibration or stirring.

Substances transformed to fibers become water insoluble aggregates.

In particular, undegraded silk protein (fibroin and/or sericin) tends to form gel (soft crystal containing water) in solution even if there is no shear.

An aqueous solution of silk protein having a molecular weight not lower than 200,000 daltons dissolved with a neutral salt becomes gel during desalting.

The gel gradually hardens, and it becomes harder when it is stirred.

Fine fiber formation easily takes place by a slight shear as described above, which causes to lower availability (touch, extensibility) of ointment and cosmetics (cream, emulsion, conditioner, and the like), resulting in poor applicability to skin care materials.

For example, when an aqueous solution of undegraded fibroin or an aqueous solution of fibroin having a molecular weight larger than ca. 300,000 daltons is lightly rubbed on hands, water insoluble aggregates of about 0.5 to 2 mm are easily formed. Even if it has a molecular weight of about 200,000 daltons or larger, aggregates are formed when it is rubbed hard, presenting lack of extensibility.

On the other hand, as the molecular weight of silk protein decreases, fiber formation by friction and the like may not occur.

In particular, when a molecular weight of silk protein becomes lower than 200,000 daltons, particularly from 50,000 to 100,000 daltons, no fiber aggregates in a ball shape are not formed even if the aqueous silk protein solution is rubbed hard. For this reason, the silk protein can become an excellent material in physical properties as a material for cosmetics or the like.

However, in silk threads for silk fabric and the like obtained by conventional cocoon processing, the H-chain of fibroin cannot be confirmed and the L-chain thereof is degraded to a level hardly confirmed.

The cell growth-promoting activity of such fibroin is about half of or less than half of undegraded fibroin.

The function of cell growth of silk protein is decreased to less than or equal to one-half of that of undegraded silk protein. However, fibroin and sericin have been used as their molecular weights were reduced during the silk manufacturing processes or the like.

In other words, the conventional uses of silk fibroin and sericin were aimed at their easy use and availability rather than their cell growth properties, and fibroin and sericin having molecular weights lower than 200,000, mainly less than 100,000, have been used.

[Patent Literature 1]
Kokoku (Jpn. examined patent publication) No. 40-24920
[Patent Literature 2]
Kokai (Jpn. unexamined patent publication) No. 62-415
[Patent Literature 3]
Kokoku (Jpn. examined patent publication) No. 1-44320
[Patent Literature 4]
Kokai (Jpn. unexamined patent publication) No. 1-254164
[Patent Literature 5]
Kokai (Jpn. unexamined patent publication) No. 1-256351
[Patent Literature 6]
Kokoku (Jpn. examined patent publication) No. 4-202435
[Patent Literature 7]
Kokoku (Jpn. examined patent publication) No. 5-83292
[Patent Literature 8]
Kokoku (Jpn. examined patent publication) No. 6-4679
[Patent Literature 9]
Kokai (Jpn. unexamined patent publication) No. 8-143595
[Patent Literature 10]
Kokai (Jpn. unexamined patent publication) No. 11-139986
[Patent Literature 11]
Kokai (Jpn. unexamined patent publication) No. 11-276876
[Patent Literature 12]
U.S. Pat. No. 2,997,758
[Patent Literature 13]
U.S. Pat. No. 2,990,239
[Patent Literature 14]
Patent application No. 2002-230656
[Patent Literature 15]
Kokai (Jpn. unexamined patent publication) No. 2001-163899
[Patent Literature 16]
patent application No. 2001-180169 (WO02/102845A1 WO publication)
[Patent Literature 17]
Kokai (Jpn. unexamined patent publication) No. 2002-128691
[Nonpatent Literature 1]
By H. Yamada et al.: Materials Science & Engineering C, 14, P. 41–46 (2001)
[Nonpatent Literature 2]
K. Tsubouchi, H. Yamada, Y. Takasu: The Japanese Society of Sericulture Science academic journal Vol. 71, No. 1, P. 1–5 (2002)

SUMMARY OF THE INVENTION

An object of the present invention is to provide polypeptide compositions originating from silk protein which has not only excellent cell growth-promoting activity associated with undegraded fibroin and sericin, the fibroin H-chain and L-chain, or the a component of sericin, but also excellent touch, extensibility or the like inherent in fibroin and sericin having a molecular weight lower than 200,000.

Particularly, it is an object to utilize an aqueous solution of the polypeptides originating from silk protein having excellent characteristics as above as materials for medicament, quasi drug, cosmetics, etc., materials for food, and the like.

The present inventors previously found that peptide chains from specific sites of silk fibroin have a cell growth-promoting function, and accumulated knowledge that peptide chains having specific amino acid sequences in one or more than one peptide chains selected from the respective peptide chains of the N-terminal portion (I), the noncrystalline portion (A) and the C-terminal portion (a) constituting the H-chain of silk fibroin from the domesticated silkworm, and the peptide chains of the noncrystalline portions of the silk fibroin from *Antheraea yamamai* have a cell growth-promoting function, and these findings have been applied for patent.

Based on the knowledge, it was found that the cell growth-promoting function of silk protein is not much lost as long as peptide chains having specific amino acid sequences which are associated with the above cell growth-promoting function remain even if a molecular weight of silk protein is reduced to 200,000 or less, thus leading to the completion of the present invention.

Namely, a first feature of the present application provides a method for producing functional polypeptide compositions originating from silk protein having an average molecular weight not lower than 10,000 and not higher than 200,000 and being excellent for cell growth-promoting activity, extensibility and the like, wherein (1) a raw silk protein material from the domesticated silkworm or *Antheraea yamamai* is solubilized in an aqueous solution of neutral salt, in which the raw silk protein material has an average molecular weight larger than 200,000 and at least a part or the whole of the H-chain and L-chain of silk fibroin and sericin a remains undegraded in the case of the raw silk protein material from the domesticated silkworm, and (2) the solution is then treated with a peptide bond-cleaving agent to cleave peptide bonds of silk protein between specific amino acid residues.

A second feature of the present application provides a method for producing the functional polypeptide compositions originating from silk protein according to the above first feature, wherein the raw silk protein material is the one consisting of one or more kinds selected from cocoon filaments spun by the domesticated silkworm or by *Antheraea yamamai*, raw silk and silk threads that are a processed material of cocoon filaments, and undegummed material, half-degummed material and degummed material of silk fabric and textile.

A third feature of the present application provides a method for producing the functional polypeptide compositions originating from silk protein according to the above first feature, wherein the aqueous solution of neutral salt of the raw silk protein material is treated with a peptide bond-cleaving agent and then the obtained polypeptide composition is subjected to a desalting process.

A fourth feature of the present application provides a method for producing the functional polypeptide compositions originating from silk protein according to the above first feature, wherein the peptide bond-cleaving agent is an enzyme, hydroxylamine or a dilute acid.

A fifth feature of the present application provides a method for producing the functional polypeptide compositions originating from silk protein according to claim 1, wherein the peptide bond-cleaving agent is hydroxylamine.

A sixth feature of the present application provides a method for producing the functional polypeptide compositions originating from silk protein according to claim 1, wherein the peptide bond-cleaving agent is an enzyme selected from lysyl endopeptidase, chymotrypsin, papain, pepsin, trypsin and thermolysin.

A seventh feature of the present application provides a method for producing the functional polypeptide compositions originating from silk protein according to claim 1, wherein the peptide bond between specific amino acid residues is Asn-Gly bond.

An eighth feature of the present application provides a method for producing the functional polypeptide compositions originating from silk protein according to claim 1, wherein the functional polypeptide compositions originating from silk protein having an average molecular weight not lower than 10,000 and not higher than 200,000 and being excellent for cell growth-promoting activity, extensibility and the like are in an aqueous solution form.

A ninth feature of the present application is an aqueous solution of functional polypeptides originating from silk protein having an average molecular weight not lower than 10,000 and not higher than 200,000 and being excellent for cell growth-promoting activity, extensibility and the like, where the functional polypeptides are obtained by the processes that (1) a raw silk protein material from the domesticated silkworm or *Antheraea yamamai* is solubilized in an aqueous solution of neutral salt, in which the raw silk protein material has an average molecular weight larger than 200,000 and at least a part or the whole of the H-chain and L-chain of silk fibroin and sericin a remains undegraded in the case of the raw silk protein material from the domesticated silkworm, and (2) the solution is then treated with a peptide bond-cleaving agent to cleave peptide bonds of silk protein between specific amino acid residues, followed by subjecting to a desalting process.

A tenth feature of the present application provides a method for using functional polypeptides originating from silk protein for medicament, quasi drug and cosmetics material for skin care via the processes that (1) a raw silk protein material from the domesticated silkworm or *Antheraea yamamai* is solubilized in an aqueous solution of neutral salt, in which the raw silk protein material has an average molecular weight larger than 200,000 and at least a part or the whole of the H-chain and L-chain of silk fibroin and sericin a remains undegraded in the case of the raw silk protein material from the domesticated silkworm, (2) the solution is then treated with a peptide bond-cleaving agent to cleave peptide bonds of silk protein between specific amino acid residues, followed by subjecting to the desalting process to obtain an aqueous solution of functional polypeptides originating from silk protein having an average molecular weight not lower than 10,000 and not higher than 200,000 and being excellent for cell growth-promoting activity, extensibility and the like, and (3) the aqueous solution of functional polypeptides is converted into film, powder, gel, or emulsion.

DESCRIPTION OF THE PREFERRED EMBODIMENT

Figure 1:
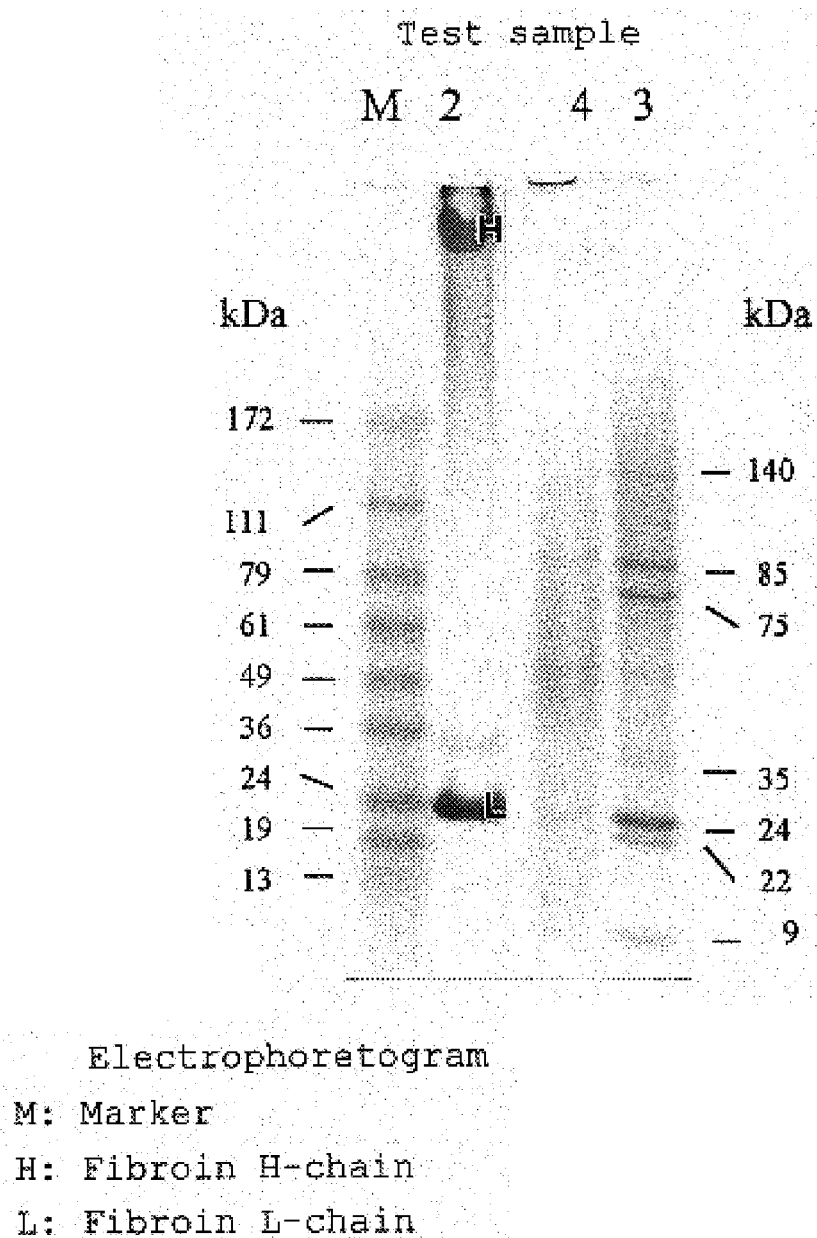
FIG. 1 is an electrophoretogram showing the results of the electrophoresis of Tert samples 2, 3, and 4.

The functional polypeptide compositions originating from silk protein of the present invention are prepared basically through the following processes (1) to (3):

(1) Undegraded silk proteins from the domesticated silkworm or *Antheraea yamamai* or a raw silk protein material having an average molecular weight not lower than 200,000 and at least a part or the whole of the H-chain and L-chain of silk fibroin and sericin a from the domesticated silkworm that remains undegraded, is solubilized in an aqueous solution of neutral salt.

(2) Next, a peptide bond-cleaving agent (enzyme, hydroxylamine, or dilute acid) is added to the above aqueous solution of neutral salt of silk protein for treatment, and the peptide bonds between specific amino acid residues (Asn-Gly bond) of silk protein are cleaved to generate reduced molecular weight polypeptides having an average molecular weight not lower than 10,000 and not higher than 200,000.

(3) The aqueous solution of neutral salt of the reduced molecular weight polypeptides having an average molecular weight not lower than 10,000 and not higher than 200,000 is subjected to a desalting process to purify.

The resulting aqueous polypeptide solution is converted to a film or powder form in accordance with the intended use or used in a gel or emulsion form and the like.

Since the raw silk protein material and the conditions for cleaving the specific peptide bonds are important factors in the present invention, first of all, this aspect will be described in detail hereinafter.

For making use of the cell growth-promoting activity of silk protein, the raw material to be used is silk protein in which the H-chain and L-chain of fibroin and the sericin a component remain.

These silk proteins are cleaved between specific amino acid residues to decrease the molecular weights of silk proteins.

In other words, this aim is that complicated cleavages of peptide bonds in silk protein do not occur or occur as little as possible.

It is preferred to use an enzyme or an alternative chemical that cleaves silk protein between specific amino acid residues.

In general, cleavage of proteins by proteinases is carried out under mild conditions, and therefore, it is said that the modification of side chains of amino acids does not occur.

At the same time, complicated fragmentation due to nonspecific cleavages may also be avoided.

Accordingly, proteolysis up to amino acid level or a level close to that rarely happens.

Such proteinases include:

lysyl endopeptidase, serine protease, metalloendopeptidase, arginyl endopeptidase, metalloprotease, chymotrypsin, papain, Alcalase, pepsin, rennin, pancreatin, elastase, carboxypeptidase, aminopeptidase, dipeptidase, and the like.

Besides enzymes, highly specific polypeptide cleavage methods are available for chemicals as well.

Chemicals used in a highly specific chemical cleavage method include cyanogen bromide, N-bromosuccinimide, BNPS-scatol (2-(2-nitrophenylsulfenyl)-3-methyl-3-bromoindole), dimethylsulfoxide, O-iodosobenzoic acid, hydroxylamine, dilute acid, and the like.

Reduction in molecular weight of silk protein during ordinary silk manufacturing processes gives rise to a broad band with a smear on electrophoretogram, while a sharp band in addition to silk protein components can be newly confirmed in the silk protein cleaved into lower molecules by means of an enzyme or an alternative chemical.

It is preferred that a plurality of sharp bands can be confirmed.

The silk protein thus reduced in its molecular weight retains the cell growth activity present in undegraded silk protein.

For example, the molecular weight of the H-chain of silk fibroin from the domesticated silk worm is ca. 350,000, and when the H-chain is cleaved between specific amino acid residues, a plurality of new bands with molecular weights lower than that of the H-chain appear on an electrophoretogram as sharply as that of the original H-chain.

In other words, it is important that, on an electrophoretogram, only a broad band with a smear does not appear as in the case of the molecular weight reduction of silk protein during ordinary cocoon processing, but a single band or preferably a plurality of bands (2 or more) appear as sharply as those of the H-chain and L-chain.

Generally, molecular weights of enzymes are larger than 10,000 or so.

On the other hand, molecular weights of the chemicals having specificity toward peptide cleavage are smaller than 10,000 or so.

It is preferred for solving the problem that the molecular weight of an agent to be used for cleavage of peptide bonds of silk protein is low.

For example, when silk protein and the cleavage agent are separated from each other by dialysis, the molecular weight of the cleavage agent lower than ca. 10,000 makes it readily possible to separate the cleavage agent from the cleaved polypeptides originating from silk protein by their molecular weights, because the molecular weights of the cleaved polypeptides originating from silk protein are mostly larger than ca. 10,000.

From this point, cleavage by an agent having a molecular weight lower than ca. 10,000 is preferred to that by an enzyme in order to uniformly cleave peptide bonds of silk protein.

Hydroxylamine ($NH_2OH$) and dilute acids are particularly preferred.

Enzymes have molecular weights larger than ca. 10,000, and after cleaving peptide bonds with enzymes, they may be denatured and inactivated.

Enzymes are proteins, and therefore, they are denatured, for example, by treating at a high temperature (ca. 90 degrees C.). This method varies to some extent depending on each enzyme used, and even if the inactivated enzyme is contained in the polypeptides originating from silk protein, there is no problem in the function as a skin care material.

Next, after peptide bonds of silk protein are thus cleaved between specific amino acid residues, the average molecular weight of the cleaved peptides should desirably be lower than 200,000 so that aggregates may not be formed from their aqueous solution by shearing due to friction, vibration, and the like.

In the molecular weight range of 150,000 to 200,000, aggregates may hardly be formed by gentle shearing. Further, the molecular weight is preferably lower than 150,000.

In the molecular weight range of 10,000 to 150,000, aggregates may hardly be formed even by strong shearing.

On the other hand, the molecular weight is higher than 10,000, preferably higher than 40,000 so that gel formation may efficiently take place after dialyzing the aqueous solution of the cleaved polypeptides originating from silk protein and a noncrystalline film may readily be formed and further have strength and flexibility.

Thus in the present invention, the molecular weights of silk protein are reduced to from 10,000 to lower than 200,000, preferably from 40,000 to 150,000, by using an enzymic cleavage method or a chemical cleavage method for peptide bonds without deteriorating the cell growth-promoting function present in the H-chain and L-chain of fibroin and the a component of sericin, and an aqueous solution of the polypeptides originating from silk protein from which no aggregates are formed even when the solution is sheared by friction and the like and which is excellent in touch is prepared and used for a skin care material.

Further, this is converted into powder, film, gel, and the like or emulsified to provide a wound-covering material and a material for cosmetics.

The cleavage of peptide bonds may be carried out at any stages of the solubilized material present with a neutral salt, during or after dialysis of the solubilized material.

It is preferred that the agent to cleave peptide bonds acts when silk protein is in a dissolved state (silk protein is in a noncrystalline or amorphous state in the solution).

In addition, a plurality of cleavage agents may be used.

It is preferred that enzymes are inactivated after cleavage when used as a cleavage agent.

Hereinafter, the foregoing method will be described in detail.

A. Raw Material

Generally, the silkworm secretes silk into the glandular lumen in the body, and this silk is called liquid silk.

The liquid silk of the domesticated silkworm is composed of fibroin and sericin (these are called silk protein), and the liquid fibroin of the domesticated silkworm has a molecular weight of ca. 370,000 [Tasiro Yutaka and Otsuki Eiichi, Journal of Cell Biology, Vol. 46, P1 (1970)].

This is called undegraded fibroin.

Further, the fibroin with the molecular weight of 370,000 is separated into ca. 350,000 molecular weight unit (H-chain) and ca. 25,000 molecular weight unit (L-chain).

Sericin is composed of 4 components, and the molecular weight of the a component excellent for cell growth-promoting activity is 400,000 (see Patent literature 18).

Sericin having this size of molecular weight is called undegraded sericin.

Here, cocoon filaments consisting mainly of sericin, or 99% or more sericin made by the sericin silkworm (e.g., Sericin Hope) may also serve as a raw material.

Although the sericin silkworm is a mutant of the domesticated silkworm, there is no difference between normal and mutant sericin proteins.

On the other hand, silk protein from wild silkworm may also serve as a raw material.

The wild silkworms belonging to the genus *Antheraea* such as *Cricula trifenestrata, Samia cynthia ricini, Antheraea pernyi* (including *Antheraea mylitta* and the like), *Antheraea yamamai* form similar silk protein components.

For example, in the silk protein from *Cricula trifenestrata* [H. Yamada and K. Tsubouchi, International Journal of wild Silkmoth & Silk, Vol. 6, P. 47–51 (2001)], fibroin shows a physical property of 350,000 molecular weight where ca. 180,000 molecular weight units are bound via S—S bonds.

On the other hand, sericin is formed with the molecular weight of ca. 400,000.

The silkworm spins liquid silk at the time of cocooning to make a cocoon (consists of cocoon filament and pupa).

In the cocoon filament, there exist fibroin at the center and sericin on the periphery, and it is known that their existing ratio is 70–80% (fibroin):20–30% (sericin).

Raw silk is made by spinning several to several tens of cocoon filaments.

Fabric woven with raw silk is called raw silk fabric.

The raw material for the present invention may include all protein fibers spun by silkworm species such as domesticated silkworm and wild silkworm. The protein fibers are, for example, cocoon filaments, raw silk, silk fabrics and knits, silk threads (fibroin fiber), left-over threads of the above or their undegummed material, half-degummed material and degummed material, fiber, powder, film, and the like.

However, it is required for these raw materials that a part of the fibroin H-chain, sericin a, their corresponding components, or the like from the domesticated silkworm remains undegraded.

The confirmation of the presence of the fibroin H-chain and the a component is carried out by observing the presence of their corresponding bands on an electrophoretogram.

Accordingly, a raw silk protein material having a molecular weight (weight average) not lower than 200,000 is used.

A process to remove sericin from cocoon filaments, raw silk or raw silk fabric is called degumming, and the fiber after degumming is silk thread or fibroin fiber.

It should be noted that degumming is not performed for sericin silkworm cocoon.

Silk threads are prepared by drying and cooking cocoons produced by farmer engaged in sericulture, followed by reeling to make raw silk, and then the raw silk or raw silk fabric is degummed to yield silk threads or silk fabric.

Flocks generated from these processes are leftover threads.

Cocoon drying is carried out by drying cocoons with a gradual decrease in temperature from 115 to 120 degrees C. to ca. 80 degrees C. over 5 to 6 hours.

Cocoon cooking is carried out by treatment with water vapor and hot water at 100 to 105 degrees C. for ca. 10 min and the cocoons are filled with hot water.

When cocoons undergo such conventional production processes for raw silk (cocoon manufacturing), more than half of the fibroin H-chain is degraded.

B. Degumming

Degumming is performed to remove sericin from the raw material, and its most conventional method employs boiling in an aqueous solution containing an alkaline sodium salt and soap (alkali soap degumming).

Other methods include degumming only with an alkaline sodium salt (alkali degumming), degumming by immersion in pressurized hot water (e.g., hot water at 120 degrees C.) (high-pressure degumming), degumming with enzyme (enzyme degumming), and the like.

There is a case where degumming is carried out by boiling only in water, but it is not common because a larger proportion of sericin is left behind. Silk threads are obtained by such degumming.

However, when raw silk is degummed with common alkali soap (for example, degumming for 2 hours at 95 to 99 degrees C. in an aqueous solution of 0.05% sodium carbonate), the H-chain and L-chain of fibroin are largely degraded, giving rise to reduction in their molecular weights to ca. 50,000 to 100,000.

When peptide bonds of silk proteins are heterogeneously cleaved by the conventional cocoon manufacturing processes as above, which results in the reduction in molecular weight, the cell growth-promoting activity of silk protein is decreased, and therefore, it is necessary in the present invention to avoid the molecular weight decrease caused by the conventional processes.

The case where degumming is not performed is called undegummed, and the case where degumming is not complete is called half-degummed. Although a half-degummed material is also usually called silk thread, it is not called fibroin fiber.

Fibroin fiber herein means more than 99% fibroin.

These are also parts of cocoon manufacturing processes.

The aqueous alkaline solution used for degumming the raw material in the present invention includes aqueous solutions of alkaline sodium salts such as sodium carbonate, sodium carbonate, sodium silicate, sodium metasilicate, sodium phosphate, sodium hydroxide.

In the case of alkali degumming, an aqueous solution of sodium bicarbonate is preferred because it provides an appropriate buffer effect.

Further, sericin may remain in the degumming in the present invention.

This corresponds to half-degumming or undegumming.

Furthermore, fibers from sericin silkworm cocoon may be added at the time of solubilization in order to increase the proportion of sericin.

What is important is that the H-chain of fibroin and the a component of sericin remain in the raw material.

Accordingly, a mild degumming is conducted so as to leave the a component of sericin behind in order to obtain a raw material in which sericin remains (see Patent literature 17).

For the mild degumming, for example, cocoon filaments are boiled, immersing in near neutral water (pH 6 to 8) for ca. one hour or are subjected to another treatment corresponding to this.

For example, when sodium bicarbonate is used, its concentration is adjusted to approximately 0.05%, and the cocoon filaments are boiled for ca. 10 min with well stirring.

On the other hand, when most of sericin is removed (more than 99% fibroin), degumming is carried out such that the H-chain of fibroin may remain undegraded as much as possible (see Patent literature 15).

For example, when the cocoon filaments are degummed by boiling in an aqueous solution of 0.05% sodium carbonate, the degumming is carried out approximately within 30 min, preferably within ca. 10 min.

In an alternative case, conditions corresponding to this are applied.

C. Solubilization of Raw Material

The polypeptides originating from silk protein of the present invention are obtained by solubilizing the above raw material as follows:

The neutral salt as a solubilizer for raw silk threads includes, for example, calcium chloride, copper ethylenediamine, sodium thiocyanate, lithium thiocyanate, lithium bromide, magnesium nitrate, and the like.

The neutral salt is preferably in an aqueous saturated solution or at a concentration not less than 50% saturation [weight (g)/volume (ml)].

In the case where fibroin and sericin are contained, for example, cocoon filaments, undegummed material, half-degummed material, and the like are solubilized using the above neutral salt in a manner similar to that for silk threads.

On the other hand, when sericin occupies 98% or more as in the case of cocoon filaments from sericin silkworm, the solubilization is carried out with 8 M urea within ca. 10 min at 70 to 90 degrees C.

Alternatively, the solubilization may be carried out with lithium bromide at a concentration not lower than 7 M within ca. 20 min when the temperature is maintained at 45 degrees C.

At the step of solubilizing the raw material in an aqueous solution of neutral salt, an alcohol such as methyl alcohol, ethyl alcohol and propyl alcohol may be added to the neutral salt.

When calcium chloride is used as the neutral salt, the solubilization is carried out at a temperature not higher than 94 degrees C., preferably in the range of from 75 to 85 degrees C.

When lithium bromide is used, the raw material is solubilized at a temperature lower than ca. 50 degrees C. Thus, depending on the neutral salt used, the conditions for solubilization vary, and a method in which the fibroin H-chain and the a component of sericin may remain or their molecular weights may be retained at 200,000 or higher is employed for solubilization.

In the case of the above solubilization, (1) the solubilization may be accelerated by stirring.

(2) the solubilization is difficult at a lower temperature.

(3) Although a higher temperature may facilitate the solubilization, a vigorous reduction in molecular weight may take place.

The solution in which the raw material is solubilized with a neutral salt contains the neutral salt, alcohol, and so on besides fibroin or a mixture of fibroin and sericin.

From this solution, insoluble materials are first removed, and then compounds having a molecular weight lower than 10,000 are removed using a dialysis membrane or dialysis equipment.

It should be noted that compounds having a molecular weight around 5,000 may remain depending on their molecular shapes without being separated, even when a dialysis membrane for molecular separation at ca. 10,000 molecular weight cut-off level is used.

An aqueous silk protein solution is obtained by such dialysis.

In this aqueous silk protein solution, a neutral salt may be allowed to remain at 0.001 to 0.2 M.

D. Cleavage of Peptide Bonds

Cleavage of peptide bonds is carried out by adding an agent to specifically cleave peptide bonds into a solution of silk protein dissolved by a solubilizer such as the neutral salts.

In this case, a plurality of cleavage agents may be used.

Enzymes, or chemical substances such as dilute acids and hydroxylamine are used as the cleavage agent.

As the dilute acids, hydrochloric acid or sulfuric acid may be used at a concentration not higher than 2 N, and preferably formic acid is used.

In the case where hydroxylamine is used, it is added so as to become 0.1 to 3 M.

When the concentration of hydroxylamine is dilute, cleavage of peptide bonds occurs erratically, resulting in inconsistent cleavage.

When the concentration is high, the specificity of peptide bond cleavage is disturbed.

As the conditions for the cleavage, the solution is adjusted to near pH 9 (pH 8.0 to pH 10.0) with an alkali (e.g., 1 N NaOH) and treated for 4 hours (30 to 6 hours, preferably 3 to 5 hours) at ca. 45 degrees C. (30 to 50 degrees C.) to cleave the peptide bond between asparagine (Asp) and glycine (Gly) in silk protein.

After the cleavage treatment, pH is adjusted to 2 to 3 with an dilute acid (e.g, formic acid) to stop the reaction.

Thus, several polypeptide fragments cleaved specifically between Asn and Gly in silk protein are obtained.

In the mean time, the amino acid sequences of silk fibroin precursor protein are registered for the H-chain as GenBank No. P05790 and for the L-chain as GenBank No. P21828.

The H-chain is composed of repetition of a part called crystalline portion mainly consisting of glycine (G), alanine (A) and serine (S), and a part called noncrystalline portion abundant in other amino acid residues.

The area occupied by the crystalline portions in the H-chain is very large, and the crystalline portion is sometimes divided into a portion having relatively high crystallinity and a portion having relatively low crystallinity. Both of these are composed mainly of a repetition of (G-X) (where X represents mainly Ala, Ser, Tyr and Val), and therefore these are considered as a crystalline portion without being distinguished here.

The number of amino acid residues in the noncrystalline portions is from 28 to 32, and there are 11 noncrystalline portions in the H-chain. Among them, 8 portions contain Asn-Gly bond.

Accordingly, if the fibroin precursor is accurately cleaved at Asn-Gly bond in the 8 portions, it is calculated that a group of 9 fragments having 688, 1259, 985, 644, 539, 391, 347, 607, and 378 amino acid residues will be formed.

It should be noted that it is not known how far the amino acid residues in the initial peptide on the N-terminal side of fibroin precursor are involved in constituting cocoon filament protein.

In addition, the fragment having 116 amino acid residues on the C-terminal side is bound to the L-chain via S—S bond.

Accordingly, even if 100% of Asn-Gly bond is cleaved among the 9 fragments, the fragment having 688 residues gives rise to fragments with smaller number of residues and the fragment having 116 residues gives rise to a fragment with more residues.

Given that the molecular weight of one amino acid residue is ca. 110, the molecular weights of most of these fragments fall into a molecular weight range of ca. 40,000 to 100,000, and 9 sharp bands appear on an electrophoretogram in that range.

However, it is acceptable that one or more bands, other than each component to constitute silk protein, as sharp as the latter appear on an electrophoretogram and their average molecular weights fall in 10,000 to lower than 200,000 as the result of 50% or more cleavage of Asn-Gly bond, even if 100% of that bond is not cleaved.

For the cleavage of peptide bonds with enzymes, lysyl endopeptidase, chymotrypsin, papain, pepsin, trypsin, thermolysin and the like are preferred.

In the case of lysyl endopeptidase, peptide bond is specifically cleaved on the carboxyl side of lysine residue.

Silk protein is treated with an enzyme in a state of an aqueous solution or while solubilizing in an aqueous solution of 4 M or lower urea.

Enzymes are added at 1% (weight) of silk protein, followed by treatment at pH 8.0 to 10 for 30 min to 4 hours at 30 to 40 degrees C.

Furthermore, this enzyme (lysyl endopeptidase) becomes rather unstable at 50 degrees C. or higher and inactivated at 70 degrees C. or higher.

Important points in the cleavage of peptide bonds in silk protein are:

1) cleaved silk protein fragments retain the excellent cell growth-promoting activity of undegraded silk protein. In other words, the cell growth rates of polypeptides originating from silk fibroin and sericin are not lower than 50% of that of undegraded fibroin and undegraded sericin, respectively;

2) the solution of polypeptides does not form aggregates due to shearing such as friction; and further preferably, 3) the solution of polypeptides is converted into gel within several days (1 to 7 days) when left standing.

To fulfill these conditions, the molecular weights of the whole cleaved fragments should fall mostly within 10,000 to 200,000 and sharp bands other than each component constituting undegraded silk protein should be observed in a molecular weight range lower than 200,000 on an electrophoretogram.

E. Preparation of Aqueous Solution of Polypeptides Originating from Silk Protein After the cleavage treatment for the peptide bonds, substances other than the polypeptides originating from silk protein are removed from the solution by desalting and the like.

In the case where the peptide bonds are cleaved by an enzyme, the aqueous solution of polypeptides originating from silk protein is heated to 70 to 90 degrees C. after desalting, thereby making the enzyme inactive.

The desalting may be carried out in a column (Sephadex G-25).

In the case where dialysis is carried out against water, the dialysis is performed by changing external dialysis fluid of 50 volumes of water 4 times or more every 2 to 4 hours, or performed with the use of another equivalent method.

In such a way, the aqueous solution of polypeptides originating from silk protein in which an excellent cell growth-promoting activity of the undegraded silk protein is retained even though the molecular weight of silk protein is reduced and from which aggregates are not easily formed by shear can be obtained.

For the cleavage of the peptide bonds, a cleavage agent may be added to the aqueous silk protein solution during desalting.

Further, the cleavage agent may be added to the aqueous silk protein solution after desalting.

The method of cleavage may vary depending on cleavage agents. Whatever the cleavage agent may be, it is required for the salt, the cleavage agent (diluted acid or $NH_2OH$) or the like to be removed by dialysis or the like after the cleavage. In the case where the cleavage agent is an enzyme, it is preferred to inactivate the enzyme.

For the judgment of desalting, when calcium chloride is used as a neutral salt, a drop of silver nitrate was dropped into a portion of the external dialysis fluid. When the dropped part hardly turned to white, the desalting was considered to be completed. Further, the judgment may be carried out by conductivity measurement of the external dialysis fluid.

F. Preparation of Film, Powder and Gel

Film, powder, gel and the like are made from an aqueous solution of polypeptides originating from silk protein which has been dissolved in a noncrystalline state.

The obtained film, powder, gel and the like are used for materials for skin care.

1) Film Formation

The aqueous polypeptide solution described above in E in which specific polypeptide bonds of silk protein have been cleaved by a cleavage agent for peptide bonds is put on a plate and air-dried to yield film.

It is possible to vary the film thickness by changing the concentration of the aqueous polypeptide solution, the volume of the aqueous polypeptide solution per unit area at the time of putting the solution onto the plate, and the like.

When making noncrystalline film, the film should have a thickness of 100 μm, and preferably not larger than about 60 μm.

If the thickness is large, it takes time to dry the film, leading to its crystallization.

In particular, the noncrystalline film is excellent for skin care materials such as wound-covering.

On the other hand, the film may be crystallized; however, the crystallized film cannot be used for a wound-covering material.

If the non-crystallized film or the crystallized film obtained by the way described above is ground, it becomes noncrystalline powder or crystalline powder of the polypeptides originating from silk protein.

2) Powder Formation

Noncrystalline powder can be obtained by not only grinding the film described in F. 1), but also spray drying or freeze drying the aqueous polypeptide solution described in E, followed by precipitating by grinding, stirring, adding alcohol, freeze treatment or the like, and then by drying, grinding or the like.

3) Gel Formation

For gel formation, the aqueous solution of polypeptides originating form silk protein is preferred to be left (standing still) as it is.

It is assumed that when the concentration of polypeptides exceeds a certain level in aqueous gel, hydrogen bonds are formed between a polypeptide chain and another adjacent polypeptide chain containing water between them and these chains are loosely bound together to form a three-dimensional mesh, whereby gel formation takes place.

Gel formation is crystallization of polypeptide (β) containing much water and it is regarded as aqueous gel.

This aqueous gel is so fragile that the gel state is easily disrupted by an external force.

A certain kind of such gel has a property that a part of the gel is dissolved in water by stirring. Such gel is referred to as aqueous gel.

In order to make aqueous gel, when an aqueous solution of polypeptides originating from silk protein is left as it is, gel formation is accelerated by making the temperature higher than room temperature (below ca. 30 degrees C.), whereas if the temperature is higher than or equal to 100 degrees C., reduction in the molecular weight tends to occur.

Further, it is advisable to avoid boiling the aqueous polypeptide solution because shear is applied to the polypeptide.

For gel formation temperature, 40 to 90 degrees C. is desirable and 50 to 80 degrees C. is preferable.

Furthermore, the higher the concentration of the aqueous solution of polypeptides originating from silk protein is, the earlier the gel formation occurs. Therefore, a desirable concentration thereof is not less than 0.1% and preferably not less than 3%.

On the other hand, the concentration must be less than 25%.

The reason why the concentration must be less than 25% is that the polypeptide cannot be converted into a liquid state during the processes of dissolving the raw material, cleaving the peptide bonds, desalting and the like, which makes it impossible to carry out these processes effectively.

The desirable concentration of the aqueous polypeptide solution is 0.1 to 15% and preferably 3 to 10%.

Aqueous gel of the aqueous solution of polypeptides originating form silk protein can be obtained by, for example, an isoelectric point method, a method in which crystallization of polypeptide in an aqueous polypeptide solution is slightly promoted, and the like. However, if the aqueous polypeptide solution is used for skin care materials, it is preferred to leave the solution as it is to transform into gel.

G. Emulsification of Aqueous Solution of Polypeptides Originating from Silk Protein or Its Aqueous Gel It is possible to emulsify the above aqueous polypeptide solution and its aqueous gel by adding an oil component for them, followed by stirring.

The oil component used for emulsification includes vegetable oils such as olive oil, camellia oil, avocado oil, coconut oil, sunflower oil, persic oil, palm oil and castor oil, and animal oil, waxes and the like such as jojoba oil and propolis, oil components such as oil and waxes described in the standards of cosmetic ingredients.

There is not so big difference in properties of emulsion among the kinds of oil components.

1) Emulsification of Aqueous Solution of Polypeptides Originating from Silk Protein It was found that the aqueous solution of polypeptides originating from silk protein can be used for an emulsifier.

As to the emulsification, an aimed emulsified material can be prepared by appropriately adjusting the proportion of the oil component relative to the concentration and the volume of the aqueous polypeptide solution.

There are various methods of emulsification by mixing an aqueous polypeptide solution and an oil component including stirring method, grinding-mixing method and the like; however, any method can be used.

It is desirable to use various machines for emulsification depending on the concentration of the aqueous polypeptide solution and the proportion of oil.

The viscosity of an emulsified material varies depending on the concentrations of the aqueous solution of polypeptides originating from silk protein.

If the concentration of the aqueous polypeptide solution is low, its cell growth activity is low.

Accordingly, the concentration of the aqueous polypeptide solution for emulsification is not lower than 0.1%, and preferably not lower than 0.5%.

On the other hand, when the concentration of the aqueous polypeptide solution is high, spreadability (extensivility) on the skin becomes poor, resulting in lowering in availabilities.

Thus, its desirable concentration is not higher than 15% and preferably not higher than 10%.

If the concentration of an aqueous solution of polypeptides originating from silk protein is low (not higher than ca. 3%), an emulsified material becomes liquid, which is available for emulsion.

As the concentration of the aqueous polypeptide solution becomes higher (not lower than ca. 3%), the solution becomes viscous, which is available for cream and ointment.

The facts that if the concentration of an aqueous polypeptide solution is low, its cell growth activity is low, and that if the concentration of an aqueous polypeptide solution is high, spreadability becomes low, and the like are applicable to the emulsification of aqueous gel described next.

2) Emulsification of Aqueous Polypeptide Gel

It has been found that aqueous gel of polypeptides originating from silk protein acts as an emulsifier when it is mixed with an oil component.

The emulsifying method is the same as that in emulsification of the aqueous polypeptide solution described in 1).

When the concentration of polypeptide in a gel state becomes about 6% or higher, it becomes difficult to mix the gel and an oil component and stir the mixture.

As the concentration becomes higher, addition of water at the time of stirring facilitates stirring and emulsification.

Water is required in 1 to 2 weights of the polypeptides.

That is, it is desirable to add 5 to 20 g of water to 100 g of gel at 10% concentration and stir them.

Compared to the case of emulsification of an aqueous polypeptide solution, it is industrially disadvantageous to emulsify an aqueous polypeptide solution after gel formation because there are many gel formation processes.

However, when an aqueous polypeptide gel is emulsified, there is an advantage that a proportion of oil component smaller than that for emulsification of an aqueous polypeptide solution suffices to emulsify.

In other words, when water contents are the same, the use of aqueous gel makes it possible to vary the proportion of an oil component and the polypeptide more widely than the use of an aqueous polypeptide solution, resulting in an advantage that emulsified materials having different properties can be obtained.

It is assumed that all the polypeptide chains are not necessary to be bound to an oil component because the polypeptides have already been intermolecularly bound loosely one another due to gel formation of the aqueous polypeptide solution.

It goes without saying that oil components such as oil and wax, pH adjuster, preservative, viscosity improver, moisturizer, germicide, anti-inflammatory agent, dye, aroma chemical, antioxidant, ultraviolet absorbent, vitamin, organic or inorganic powder, alcohol, carbohydrates etc., or components generally used for skin care for ointment, cosmetics etc., can be mixed as necessary in the emulsified materials of the polypeptides originating from silk protein of the present invention within the range where the action and effectiveness of the present invention are not impaired.

H. Use of Polypeptides Originating from Silk Protein

Polypeptides originating form silk protein retaining the excellent cell growth-promoting activity of undegraded silk protein can be obtained in the forms of aqueous solution, film, powder, gel and emulsion by the above methods.

Those vitalize skin cells and promote their growth. For these reasons, they are particularly effective in the following usage.

(1) Coating Material

The polypeptides originating from silk protein can be used for a coating material for silk whose cell growth-promoting activity has been reduced (for example, crystalline silk powder obtained by alkali treatment) and other materials (for example, body powder such as talc, organic and inorganic powder such as ceramic powder, parts with which a living body comes into contact such as glasses, wrist watch, ring, pierced earring, syringe needle, and medical instruments such as surgical tools which come into contact with a living body).

When the polypeptides are used for coating materials, the properties of the materials are improved by coating the surfaces of the materials with polypeptides originating from silk protein by immersing the materials in an aqueous solution of polypeptides originating from silk protein for adding a function of cell growth promotion to the original characteristics of the materials.

To add such a function, the membrane thickness is 0.01 to 3 mμ and preferably 0.1 to 1 mμ.

To enhance adhesion of polypeptides originating from silk protein, a binder may be used for coating.

The improved powder obtained in such a manner is also excellent for body powder and foundation.

Further, when the polypeptides are used for pierced earring and syringe needle, it is possible to suppress inflammation of living body.

(2) Film

Noncrystalline film absorbs water, antiseptic solution and the like and is dissolved or partially dissolved. Therefore, the film can be used alone or in combination of fabric or film for skin care materials, adhesion to the skin or coating over the skin as a solution, or wound-covering agents.

In addition, the noncrystalline film that has absorbed water on the skin is dried in about 10 to 30 min by liberating water by body temperature and the like.

If the film is used for face mask and the like, undesired minute substances on the skin can be removed because the dried film contains undesired oil, dirt and the like on the surface of the skin. Moreover, when the film remains thinly on the skin and is not peeled off by friction, it is left as it is.

(3) Powder

The above improved powder or the powder obtained by grinding the film is used alone for wound healing or make-up, or used after being added to other wound healing drugs and cosmetics as skin care powder.

(4) Gel

Gel is used by being added to food or gelatinizer and gel food.

(5) Emulsified Material

Emulsified materials are used alone or used as an additive for wound healing agent and cosmetics for skin care.

Specifically, as materials for ointment, cream, emulsion and conditioner, emulsified materials made from polypeptides originating from silk protein of the present invention are excellent for skin cell growth promotion, touch, adhesion and spreadability.

When the polypeptides are used for emulsified materials, the polypeptides originating form silk protein, an oil component and water are mixed ranging in weight proportion in which the oil component is 1 to 20%, water is 80 to 90%, preferably the oil component is 3 to 45% and water is 55 to 97%, and more preferably the oil component is 7 to 30% and water is 70 to 93% when the concentration of polypeptides originating from silk protein is 1%.

When the concentration of polypeptides originating from silk protein is 10%, an oil component and water are mixed in the ranges where the oil component is 15 to 50% and water is 50 to 85%, and preferably the oil component is 20 to 35% and water is 75 to 80%.

Other proportions can be appropriately determined from the above composition ratios.

These composition ratios are approximately the same as those described in Kokai (Jpn. unexamined patent publication) No. 2001-364489 (see Patent literature 14).

The cell growth rates of polypeptides originating from silk protein of the present invention are not less than 50% of undegraded fibroin and are mostly not less than 75%.

On the other hand, the cell growth rates described in the above Kokai (Jpn. unexamined patent publication) No. 2001-364489 are less than 50% of undegraded fibroin; therefore, the polypeptides of the present invention is excellent for cell growth activity.

Emulsified cosmetics and quasi drugs which are producible with the use of emulsified materials according to the present invention include, for example, cleansing cosmetics (beauty soap, facial wash, shampoo, rinse, and the like), hair care products (hair dye, hair cosmetics, and the like), basic cosmetics (general cream, emulsion, shaving cream, conditioner, cologne, shaving lotion, cosmetic oil, facial mask, and the like), make-up cosmetics (foundation, eyebrow pencil, eye cream, eye shadow, mascara, and the like), aromatic cosmetics (perfume and the like), tanning and sunscreen cosmetics (tanning and sunscreen cream, tanning and sunscreen lotion, tanning and sunscreen oil, and the like), nail cosmetics (nail cream and the like), eyeliner cosmetics (eyeliner and the like), lip cosmetics (lipstick, lip cream, and the like), oral care products (tooth paste and the like) bath cosmetics (bath products and the like), and the like.

As medicament, the emulsified materials can be used for wound-covering agents such as ointment.

In order to vitalize skin cells, addition of the aqueous solution, film, powder gel or emulsified material using the polypeptides originating from silk protein of the present invention to conventional skin care materials is effective.

It goes without saying that oil components such as oil and wax, pH adjuster, preservative, viscosity improver, moisturizer, germicide, anti-inflammatory agent, dye, aroma chemical, antioxidant, ultraviolet absorbent, vitamin, organic or inorganic powder, alcohol, carbohydrates etc., or components generally used for skin care for ointment, cosmetics etc., can be mixed as necessary within the range where the action and effectiveness of the present invention are not impaired.

EXAMPLE 1

Cleavage of Asn-Gly Bonds in silk protein by hydroxylamine (NH$_2$OH), electrophoretograms of cleavage products, and measurement of average molecular weight Raw cocoons 1 week after being formed by the domesticated silkworm were used as a raw material. This is referred to as "Test sample 1".

The cocoon shells of the raw cocoons (100 g) were immersed and degummed in 4,000 g of 8 M of urea at 80 degrees C. for 7 min.

In the above step, sericin was removed by stirring well.

The weight loss (degumming loss) during the step was 24.7%.

In order to examine the remaining of sericin, the degummed cocoon shells were boiled in 4,000 g of an aqueous solution of 0.05% sodium carbonate for 60 min, resulting in degumming loss of 0.7%.

It is considered that not less than 99% of the cocoon shells after degumming in 8 M urea was fibroin fibers (silk thread).

This is referred to as "Test sample 2".

Next, 15 g of the silk threads obtained by degumming in 8 M urea were put in 200 ml of 9 M LiSCN and solubilized at room temperature (25 degrees C.).

To this solution, about 30 ml of 50% hydroxylamine was added, followed by addition of about 6 ml of 1 N NaOH to adjust its pH to 9, and then the temperature of the solution was raised to 45 degrees C. and the solution was left for 4 hours.

After this, 16 ml of 99% formic acid was added to the solution, and the solution was adjusted to pH 2 to stop cleavage of Asn-Gly bonds by hydroxylamine. The resulting solution was dialyzed against water (at room temperature).

With a dialysis membrane, UC36-32-100 (made by Sanko Junyaku Co., Ltd.), 100 volumes of water was used as an external dialysis fluid and dialysis was carried out by changing water 5 times every 3 hours.

The water was stirred well during the dialysis.

The obtained polypeptide originating from fibroin is referred to as "Test sample 3".

As is described above, 15 g of the silk threads obtained by degumming with 8 M urea was put in 200 ml of 9 M LiSCN and solubilized at room temperature.

This solution was put into a dialysis membrane and dialyzed against water. To the obtained aqueous fibroin solution, about 30 ml of 50% hydroxylamine was added in the same way as described above, followed by adjusting its pH to 9 with 1 N NaOH.

This solution was left for 4 hours at 45 degrees C. and dialyzed against water after being adjusted to pH 2 with formic acid.

Thus-obtained polypeptide originating from fibroin here is referred to as "Test sample 4".

After Test samples 2 to 4 were dissolved in 9 M LiSCN, they were substituted with 8 M urea, and S—S bonds were cleaved by 2-mercaptoethanol to make test samples for electrophoresis.

The molecular weights of fragments with cleaved Asn-Gly bonds of silk protein were measured with the use of an electrophoretogram and a gel chromatography column as follows.

Gel used for the electrophoresis was 2 to 15% acrylamide gradient gel. The gel after electrophoresis was dyed with CBB (staining solution) and the bands on the electrophoretogram were observed compared to the molecular weights of control markers.

The electrophoretogram is shown in FIG. 1.

The bands of the H- and L-chains of fibroin are clearly recognized in Test sample 2 in FIG. 1. The bands of the H- and L-chains in Test sample 3 are not recognized but several bands can be recognized as sharply as those of the H- and L-chains in the part having molecular weights different from those of the H- and L-chains.

In the case where silk threads are processed in conventional cocoon manufacturing processes, for example, silk threads are degummed by sodium carbonate and the like or in the case where silk threads are solubilized with a neutral salt such as calcium chloride, or the like, the electrophoretogram shows a smear with only a broad band, and is different from the one for Test sample 3.

As to Test sample 3, 7 clear bands can be recognized. According to their molecular weights, each band corresponds to ca. 140, 85, 75, 35, 24, 22 and 9 kDa, respectively.

In addition, a smear with broad bands is slightly recognized in the molecular weight range lower than 200,000 daltons, and most Asn-Gly bonds in fibroin are considered, from the electrophoretogram of Test sample 3, to have been cleaved.

On the other hand, the bands arising from Asn-Gly bond cleavage of Test sample 4 are not clear compared with those of Test sample 3; however, bands can be recognized at 85 and 9 kDa.

From the electrophoretograms of Test samples 3 and 4, it is understood that, when LiSCN is used as a solubilizer for silk threads, the cleavage of Asn-Gly bonds by hydroxylamine performed while silk protein is solubilized with LiSCN gives more uniform cleavage.

The molecular weight measurement was carried out with the use of a gel chromatography column (Superdex 200 Prep grade, Pharmacia). The test samples were eluded with 8 M urea/40 mM Tris-H$_2$SO$_4$ (pH 8) (0.6 ml/min), and monitored at 275 nm.

The results of weight average molecular weights of these test samples are shown in Table 1.

Test samples 2 to 4 were dissolved in 9 M LiSCN, and then put into a dialysis membrane, followed by dialyzing against water. Thus-obtained aqueous solutions of silk protein and polypeptides originating from silk protein were put onto hands and rubbed, whereby ball-shaped aggregates were formed from the aqueous solution of Test sample 2; however, there were no aggregates formed from the aqueous solutions of Test samples 3 and 4, which were excellent in touch.

TABLE 1

| Molecular weight of each Test sample | |
|---|---|
| Test sample | Molecular weight |
| Test sample 2 | 305,000 |
| Test sample 3 | 167,000 |
| Test sample 4 | 45,000 |

EXAMPLE 2

Cell Growth Activity of Polypeptides Originating from Silk Protein

The cell growth activity of Test samples 1 to 4 in [Example 1] was measured as follows.

First, each test sample was coated over cell culture dishes as follows.

In 1 ml of 9 M LiSCN, 0.01 g of each test sample was dissolved and each solution was dialyzed against 50 volumes of water 4 times to make aqueous solutions of each test sample.

One ml of 0.0025% solution of each aqueous test sample solution was put in cell culture dishes (35 mmϕFalcon), air-dried, washed with 2 ml of PBS 3 times, air-dried again, and then immersed in 70% ethanol to sterilize.

The cells used were human skin fibroblasts (made by Kurabo Industries Ltd.).

The culture medium used was the low serum culture medium for human skin fibroblast growth (made by Kurabo Industries Ltd., 10 ml of LSGS added to 500 ml of Medium 106 S).

As to the culture, the medium was added at 2 ml per dish, and 70,000 cells were inoculated and cultured for 3 days.

As to the measurement of cell number, the medium at 2 ml per dish and Alamer Blue (IWAKI) at 0.1 ml per dish were added and cultured for 2 hours at 37 degrees C., and then the reduced amount of Alamer Blue calculated from the absorbances at 570 nm and 600 nm was correlated with growing cell number.

With the growing cell numbers in the dishes not having been coated with any test samples taken as control (100%), the cell growth rates in the dishes having been coated with the test samples are shown in Table 2.

Table 2 shows that Test samples 1 to 3 all show almost the same excellent cell growth-promoting activity.

The cell growth rate of Test sample 4 is slightly low compared to those of the other test samples; however, its rate is close to those of Test samples 1, 2 and 3, and any of them is excellent for cell growth promotion.

[Table 2]

Cell growth rates of cocoon shells (Test sample 1), silk threads (Test sample 2), polypeptides originating from silk protein treated with $NH_2OH$ during solubilization of silk threads with LiSCN (Test sample 3) and polypeptides originating from silk protein treated with $NH_2OH$ after solubilization and desalting of silk threads with LiSCN (Test sample 4)

| Test sample | Cell growth rate (%) |
|---|---|
| Control | 100 |
| Test sample 1 | 311 |
| Test sample 2 | 318 |
| Test sample 3 | 319 |
| Test sample 4 | 259 |

EXAMPLE 3

Gel Formation and Emulsification of Polypeptides Originating from Silk Protein

Portions of each aqueous solution of Test samples 2 to 4 in Example 1 were adjusted to 5% in concentration and the solutions were left at 70 degrees C.

The aqueous solution of Test sample 2 transformed into gel at the time of completion of its dialysis.

On the other hand, each aqueous solution of Test samples 3 and 4 formed gel after being left for 2 to 3 days at 70 degrees C.

When the gel material was slightly rubbed with hands, small ball-shaped aggregates were formed immediately from the gel of Test sample 2, whereas no aggregates were formed from Test samples 3 and 4.

Next, 20 g of olive oil was added to 70 g of each gel of Test samples 3 and 4, followed by stirring the mixture with a coffee mill [Personal Mill SCM-40A (made by Shibata Scientific Technology, Ltd.)] for 30 seconds, which yielded creamy emulsified materials from both of Test samples 3 and 4.

Even if these emulsified materials were applied onto the skin rubbing them hard, no ball-shaped aggregates were formed, and the materials were excellent in spreadability, adhesion, touch and the like.

EXAMPLE 4

$NH_2OH$ Treatment During Desalting of Solubilized Silk Threads with Calcium Chloride In the boiled solution (ca. 100 degrees C.) of a mixture of 4 g of sodium carbonate and 8 kg of water, 200 g of raw cocoon shells having been spun by the domesticated silkworm was immersed for 10 min to degum ("Test sample 5").

During the above steps, the mixture was stirred well.

Fifty g of the silk threads (Test sample 5) was immersed in a mixture of 160 g of calcium chloride, 133 g of ethanol and 207 g of water at ca. 80 degrees C. and stirred well.

The silk threads were solubilized in 20 min.

This solution was put in a dialysis membrane and dialyzed against water.

During the dialysis, 20 volumes of water as an external dialysis fluid was changed 3 times every 30 min.

At this point, the dialysis was in the middle and about one-half of desalting was completed.

To 100 g of the fibroin solution (ca. 6% concentration) (45 degrees C.) in the middle of dialysis was added 10 cc of 50% $NH_2OH$, followed by further addition of formic acid to adjust to pH 9.

After the solution was left as it was for 4 hours, formic acid was added to adjust to pH 2 and put in a dialysis membrane, followed by dialyzing this solution against water.

After completion of the dialysis, the aqueous solution was put on a plastic plate and dried to yield a film. This film is referred to as "Test sample 6".

The molecular weights of Test samples 5 and 6 were examined by the same method of electrophoresis as that in [Example 1].

The H- and L-chains of fibroin in Test sample 5 were confirmed as clearly as those in Test sample 2 of [Example 1].

Bands at 85, 75 and 9 kDa could be confirmed on the electrophoretogram of Test sample 6.

An aqueous solution of Test sample 6 was left at 70 degrees C. for gel formation.

When olive oil and water were added to the gel materials to emulsify as done in [Example 3], emulsified materials excellent in touch, spreadability, adhesion and the like could be obtained.

EXAMPLE 5

$NH_2OH$ Treatment of Silk Threads Solubilized with 8 M Lithium Bromide (LiBr)

Fifty g of the silk threads of [Example 4] was immersed in 400 g of 8 M LiBr at 45 degrees C. and stirred well, which allowed the silk threads to be solubilized in about 10 min.

The solution was put in a dialysis membrane and dialyzed against water to yield an aqueous fibroin solution. The temperature of this aqueous fibroin solution was raised to 45 degrees C. Fifty ml of 50% NH$_2$OH was added to this solution, followed by further addition of 1 N NaOH to adjust to pH 9, and the solution was left for 4 hours.

After that, the solution was adjusted to pH 2 by formic acid, put in a dialysis membrane, and dialyzed against water.

The molecular weights of obtained polypeptides originating from silk fibroin after the dialysis were examined by electrophoresis in a manner similar to that of [Example 1].

As the result, bands were confirmed at 85, 75, 35 22 and 9 kDa, respectively.

Further, after completion of the dialysis, a portion of this aqueous solution was adjusted to 5% concentration and left at 70 degrees C., which formed gel in 2 days.

To 50 g of the gel material was added 15 g of olive oil and the mixture was stirred with a coffee mill to yield a creamy emulsified material, which was excellent in touch, spreadability and adhesion.

Furthermore, this aqueous solution was put on an acrylic plate after the dialysis and air-dried at room temperature to form film.

The obtained film (ca. 40 μm thickness) showed water solubility (96% or more by weight was dissolved in water at room temperature) and served as a film of polypeptides originating from noncrystalline fibroin.

EXAMPLE 6

Omitted

COMPARATIVE EXAMPLE 1

Reduction in Molecular Weight by Heterogenous Peptide Bond Cleavage of Silk Sericin and Cell Growth Activity In 100 cc of 8M urea at 80 degrees C., 20 g of cocoon shell of cocoon (raw cocoon) from the domesticated silkworm was immersed for 15 min with stirring well to solubilize cocoon sericin.

The degumming loss of cocoon shell was 21.2%.

The aqueous cocoon sericin solution was put in a dialysis membrane and dialyzed against 40 volumes of water (60 degrees C.) as an external dialysis fluid.

The dialysis was carried out by changing water 8 times in 2 days.

The aqueous sericin solution after the dialysis was boiled (100 degrees C.) and sodium carbonate (Na$_2$CO$_3$) was added to make it 0.05% concentration.

At each boiling time of 0, 2, 5, 10, and 30 min after the addition of sodium carbonate, portions of the aqueous sericin solution were taken out, put in a dialysis membrane for dialysis against water to prepare test samples for molecular weight measurement.

Further, the dialyzed solution was used for test samples for cell culture.

The molecular weights and cell growth rates were obtained in the same method as those used in Examples 1 and 2.

The case where no components of silk protein were added was set as control (100%).

The results are shown in Table 3.

[Table 3]

Molecular weights and cell growth rates of sericin boiled in 0.05% aqueous sodium carbonate solution in relation to boiling time.

| Boiling time (min) | Molecular weight | Cell growth rate (%) |
| --- | --- | --- |
| 0 | 319,000 | 323 |
| 2 | 233,000 | 270 |
| 5 | 178,000 | 130 |
| 10 | 55,000 | 106 |
| 30 | 42,000 | 82 |

EXAMPLE 7

NH$_2$OH Treatment for Cocoon Shell of Sericin Silkworm

In 200 cc of 9 M LiBr, 4 g of cocoon shell of sericin silkworm (Sericin Hope) was put and stirred well at ca. 45 degrees C. to solubilize in ca. 15 min.

The solution has a significant viscosity.

One-third of this solution was put in a dialysis membrane for dialysis against water.

This solution formed gel during the dialysis within 1 day after starting the dialysis.

This gel material is referred to as "Test sample 7".

To the remaining two-third of the solution, 10 cc of 50% NH$_2$OH was added, and further 1 N NaOH was added to adjust its pH to 9, followed by dividing this solution into two. The divided solutions were left at 45 degrees C.

The pH of each solution was adjusted to 2 by formic acid 1 hour and 4 hours after being left at 45 degrees C., and each solution was put in a dialysis membrane for dialysis against water (room temperature) to desalt.

When adjusted to pH2by formic acid at 1 hour, the solution was transformed into gel at the time of completion of dialysis.

This gel material was referred to as "Test sample 8".

In the case of adjustment to pH 2 by formic acid at 4 hours, no gel formation was observed at the time of completion of dialysis.

The polypeptides in this solution were referred to as "Test sample 9".

Figure 2:
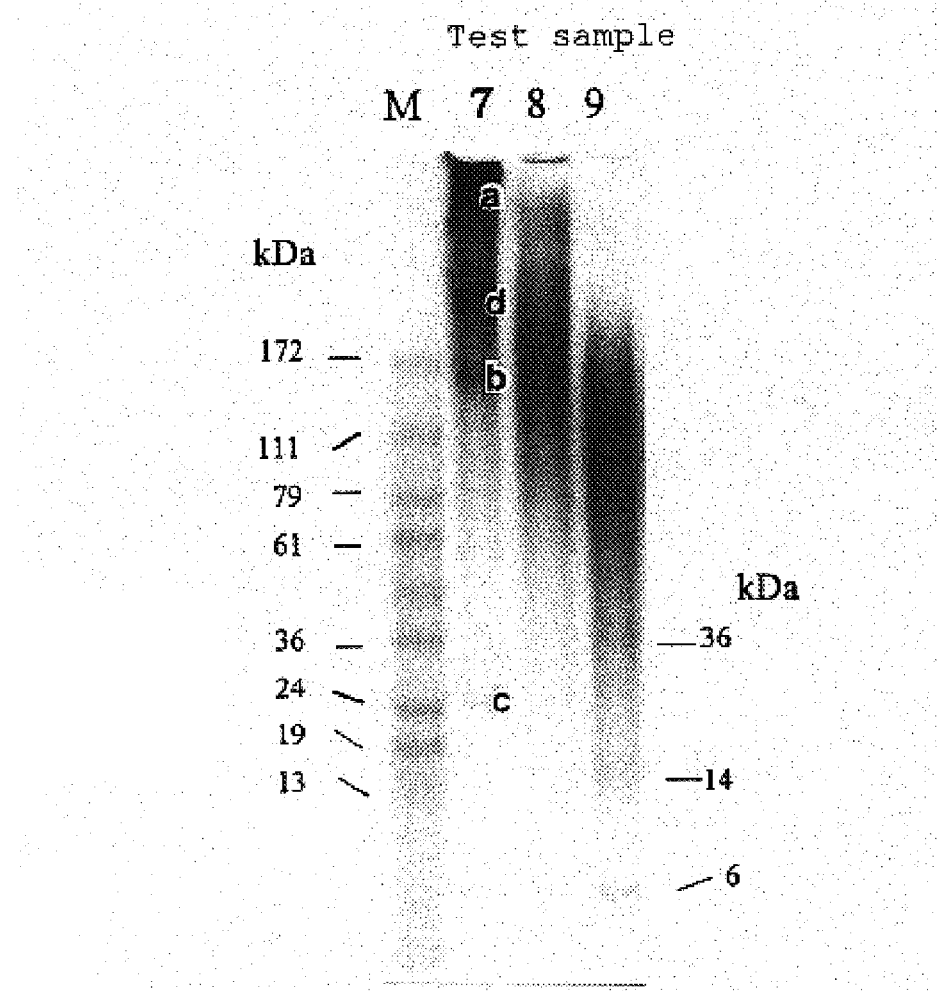
FIG. 2 is an electrophoretogram showing the results of the electrophoresis of Tert samples 7, 8 and 9.

The electrophoretogram of Test samples 7 to 9 is shown in FIG. 2.

The electrophoretogram was obtained in the same method as that in Example 1.

On the electrophoretogram of Test sample 7, each component of sericin, a, d, b, c can be confirmed.

Each component, a, d, b, of sericin cannot be confirmed in Test sample 8 and any other sharp bands also cannot be observed.

In Test sample 9, sharp bands corresponding to the portions at 36, 14, 6 kDa, respectively, can be confirmed.

When Test samples 7 to 9 during dialysis were put on the hands and rubbed, ball-shaped aggregates were formed from Test samples 7 and 8; however, no aggregates were formed from Test sample 9.

When the cell growth activity of Test sample 9 usable as functional polypeptide was measured in the same method as that in [Example 2], it showed 247% compared to the cell growth rate (%) in control set at 100%, and polypeptides originating from silk sericin excellent for cell growth promotion of fibroblasts were obtained.

When 10 g of olive oil was added to 30 g of the aqueous solution of Test sample 9 and the mixture was stirred with a coffee mill for 30 seconds, it became soft cream, which was excellent in touch, spreadability and adhesion to the skin.

EXAMPLE 8

Coating Material

Extra fine powder of crystalline silk was prepared as follows.

Raw silk from the domesticated silk worm was boiled in 0.1% aqueous sodium carbonate solution 50 times as much weight as the raw silk for 1 hour and degummed to prepare silk threads.

One hundred g of this silk threads was immersed in a solution of 50 g of sodium carbonate, 2,500 g of water and 5 g of sodium hydrosulfite, and left for 5 hours at 110 degrees C. (at 1.46 atmospheric pressure).

Then, it was washed with water and dried to grind.

Grinding was carried out with a rotatable percussion mill (made by Fuji Denki Kogyo K. K., Sample mill KI-1) attached with a filter of 1 mmφ, and further grinding was carried out with the filter attached with a wire mesh with 0.1 mm spacing.

Next, after the obtained powder was ground down by friction with an agitation grinding device (Ishikawa type), the powder was further ground with a current-type grinder (made by Nisshin Flour Milling Co. Ltd., Current jet CJ-10) to yield crystalline extra fine silk powder with an average particle diameter of 2.2 μm.

Fifty g of this crystalline extra fine silk powder was mixed with 50 g of the aqueous solution (4% concentration) of peptides originating from fibroin (Test sample 3) of the above [example 1], dried and ground.

The grinding was carried out with a rotatable percussion mill [Sample mill KI-1 (made by Fuji Denki Kogyo K.K.)] attached with a filter of 1 mmφ, and next, grinding down by friction was carried out (agitation grinding device), followed by further grinding with the filter attached with a wire mesh with 0.1 mm spacing.

The average particle diameter of the obtained powder was 2.9 μm and it was excellent in touch, adhesion and formability.

EXAMPLE 9

Cell Growth Activity of Enzymic Digest of Silk Fibroin (1) Digestion of Silk Fibroin with an Enzyme, and Subsequent Separation and Fractionation Cocoons from the domesticated silkworm were cut to remove pupae, and cocoon shells (20 g) were immersed in 8 M urea 30 times as much weight of the cocoon shells for 10 min at 90 degrees C. to remove sericin.

The extracted residue was washed with water and dried to yield fibroin.

Ten g of fibroin was immersed in 100 ml of 9 M LiSCN to be dissolved, and then 100 ml of distilled water was added, followed by centrifugation for 10 min at 3,000 rpm.

The supernatant was dialyzed against 50 volumes of water.

The dialysis was carried out with a semipermeable membrane by changing water four times every 30 min.

After dialysis, the solution was again centrifuged, and to the supernatant was added 0.1 M disodium hydrogenphosphate (pH 8.5) to adjust its pH to 7 to 8.

Chymotrypsin was added into the solution at one-hundredth amount of fibroin, and left for 1 hour at 40 degrees C.

The protein present in this supernatant was referred to as "Test sample 10".

The supernatant was determined for its protein concentration as it was.

(2) Coating on Cell Culture Dish

An aqueous solution of Test sample 10 was adjusted to 0.025% concentration by adding 70% ethanol, and 1 ml of this solution was added to a dish made of polystyrene (35 mmφ, Falcon) and air-dried.

Dishes for control contained 1 ml of 70% ethanol only and were air-dried.

(3) Cell Culture

Cells used were frozen human skin fibroblasts originating from adult human (product of Sanko Junyaku Co. Ltd.).

The culture medium used was the low serum culture medium for human skin fibroblast growth (purchased from Kurabo Industries Ltd).

Two ml of the medium was added per dish, and 80,000 cells were inoculated and cultured for 3 days.

(4) Measurement of Viable Cell Number with Alamer Blue Dye

Two ml of the medium and 0.1 ml of Alamer Blue (IWAKI) were added per dish, and after culturing for 2 hours at 37 degrees C., the viable cell number was obtained from the amount of reduced Alamer Blue dye calculated from absorbances at 570 nm and 600 nm.

The above measurement for cell growth rate was carried out as that in Example 1.

(5) Molecular Weight

The molecular weight of Test sample 10 was measured as described in Example 1.

The growth rate of human skin fibroblasts in dishes coated with Test sample 10 in comparison with control (100%) without any added components of silk protein and the molecular weight of Test sample 10 are shown in Table 4.

[Table 4]

The cell growth rate of human skin fibroblasts in dishes coated with Test sample 10 and its molecular weight

|  | Molecular weight | Cell growth rate (%) |
| --- | --- | --- |
| Test sample 10 | 55000 | 308 |

The cell growth rate in dishes coated with the silk protein component was higher compared with that of the control, showing a value similar to that with undegraded fibroin.

The protein concentration of Test sample 10 in the supernatant described in the above (1) was adjusted to 3.5%, and left standing at 80 degrees C., which was converted into gel in 3 days.

On the other hand, when this supernatant (3.5% concentration) was mixed with 30% (weight) of Test sample 9 and left standing at room temperature, gel was formed in 2 days.

When 12 g of olive oil was added and mixed with each 50 g of these gel materials, cream with good touch was obtained without forming any ball-shaped aggregates.

EXAMPLE 10

Functional Polypeptides Originating Form Silk Protein as Additive

Raw silk (150 g) was treated with a boiling liquid (ca. 100 degrees C.) of sodium carbonate (20 g), bleach (hydrosulfite: 1.5 g), sequestering agent (Clewat, Teikoku Chemical Industries Co., Ltd.: 2 g) and water (6,000 g) for 1 hour, washed with water and dried to yield silk threads (A)

The silk threads (A: 50 g) were solubilized in a solution (ca. 80 degrees C.) of calcium chloride (131 g), water (170 g) and ethyl alcohol (108 g) in 1 hour and then desalted by dialysis against water to make a fibroin solution (Test sample 11).

On the other hand, cocoon filaments of cocoons (100 g) within 5 days after silkworm spun and not having been treated by heating and the like were treated with a boiling liquid (ca. 100 degrees C.) of sodium carbonate (2 g) and water (4,000 g) for 10 min, followed by washing with water and drying to yield silk threads (B).

This silk threads (B: 20 g) were solubilized in 9 M lithium bromide (200 ml) in 30 min at 45 degrees C., 50% hydroxylamine (5 ml) was added, and further 1 N sodium hydroxide was added to adjust the solution to pH 9.

After this solution was left for 4 hours at 45 degrees C. and adjusted to pH 2 by formic acid, the obtained solution was put in a semipermeable membrane to dialyze in water, giving a fibroin solution (Test sample 12).

Test sample 12 is the functional polypeptides originating from silk protein of the present invention.

Each concentration of Test samples 11 and 12 was adjusted to ca. 5%, and 15 g of Test sample 11 and 5 g of Test sample 12 were mixed together (Test sample 13) and air-dried on a plastic plate.

The obtained film is water-soluble.

The solution in which this film was dissolved was excellent in spreadability and forming of foam.

On the electrophoretogram of Test sample 11, both H-chain and L-chain of fibroin were not confirmed and its average molecular weight was ca. 100,000.

As to silk threads B, both H-chain and L-chain of fibroin were confirmed and its average molecular weight was ca. 250,000.

As to Test sample 12, the H-chain of fibroin was not confirmed, while the L-chain was slightly confirmed. Besides those, new bands at molecular weights of ca. 50,000, 22,000, 15,000, 9,000 and so on could be confirmed.

EXAMPLE 11

Addition to Functional Polypeptides Originating from Silk Protein

Thirty g of cocoon filaments of cocoons within 5 days after silkworm spun and not having been treated by heating and the like was boiled(about 100 degrees C.) in a mixture of 0.5 g of sodium carbonate and 1,000 ml of water for 10 min to degum the silk filaments.

The degumming liquid was put in a semipermeable membrane and dialyzed against water to yield a sericin solution. (Test sample 14).

In order to use sericin as a moisturizer, 2 g of the sericin solution (Test sample 14) was added to 10 g of the fibroin solution (Test sample 12), mixed together and then air-dried on a plastic plate.

The obtained film was water-soluble.

The mixed solution and the solution in which the film was dissolved in water were excellent in spreadability and forming of foam as well as enhanced feeling of moisture on the skin.

Moreover, 1 g of squalane was added to 20 g of the fibroin solution (Test sample 12) and the added solution was mixed, followed by air-drying on a plastic plate.

The obtained film was water-soluble.

In this case too, the mixed solution and the solution in which the film was dissolved in water were excellent in spreadability and forming of foam as well as feeling of moisture on the skin.

The polypeptides originating from silk fibroin of the present invention have an average molecular weight in a range of 10,000 to lower than 200,000 and a growth-promoting activity for skin cells as excellent as that of undegraded silk protein.

Moreover, its solution does not form aggregates even when shearing such as friction is applied, which is different from undegraded silk protein, and has an excellent extensibility.

It can also be used as an emulsifier.

Thus, film, powder, aqueous solution, gel and emulsion obtained from the polypeptides originating from silk fibroin are very useful for medicament, quasi drug, cosmetics and the like as a skin care material.

The present invention relates to functional polypeptide compositions originating from silk protein excellent for cell growth-promoting activity, extensibility and the like, the production method thereof, and the use thereof as skin care materials in the fields of medicament, quasi drug, cosmetics, food and the like; however, the present invention is applicable to other biological fields as long as it does not separate from its essentials.

What is claimed is:

1. A method for producing functional polypeptide compositions originating from silk protein having an average molecular weight not lower than 10,000 and not higher than 200,000 and being excellent for cell growth-promoting activity and extensibility, comprising:

solubilizing a raw silk protein material from the domesticated silkworm or *Antheraea yamamai* in an aqueous solution of neutral salt, said raw silk protein material having an average molecular weight larger than 200,000 and at least a part or the whole of the H-chain and L-chain of silk fibroin and sericin a left undegraded in the case of the raw silk protein material from the domesticated silkworm; subsequently treating the solution with a peptide bond-cleaving agent; and cleaving peptide bonds between specific amino acid residues of silk protein.

2. The method for producing functional polypeptide compositions originating from silk protein according to claim 1, wherein the raw silk protein material is the one consisting of one or more kinds selected from cocoon filaments spun by the domesticated silkworm or by *Antheraea yamamai,* raw silk and silk threads which are processed materials of cocoon filaments, and undegummed material, half-degummed material and degummed material of silk fabric and textile.

3. The method for producing functional polypeptide compositions originating from silk protein according to claim 1, wherein an aqueous solution of neutral salt of the raw silk protein material is treated with the peptide bond-cleaving agent and then the resulting polypeptide composition is subjected to a desalting process.

4. The method for producing functional polypeptide compositions originating from silk protein according to claim 1, wherein the peptide bond-cleaving agent is an enzyme, hydroxylamine or a dilute acid.

5. The method for producing functional polypeptide compositions originating from silk protein according to claim 1, wherein the peptide bond-cleaving agent is hydroxylamine.

6. The method for producing functional polypeptide compositions originating from silk protein according to claim 1, wherein the peptide bond-cleaving agent is an enzyme selected from lysyl endopeptidase, chymotrypsin, papain, pepsin, trypsin and thermolysin.

7. The method for producing functional polypeptide compositions originating from silk protein according to claim 1, wherein the peptide bond between specific amino acid residues is Asn-Gly bond.

8. The method for producing functional polypeptide compositions according to claim 1, wherein the functional polypeptide compositions originating from silk protein having an average molecular weight not lower than 10,000 and not higher than 200,000 and being excellent for cell growth-promoting activity and extensibility are in an aqueous solution form.

* * * * *